United States Patent [19]

Utsugi

[11] 4,198,960

[45] Apr. 22, 1980

[54] APPARATUS FOR REMOVING A FOREIGN MATTER HAVING INDIVIDUALLY OPERABLE TRAPPING AND FLEXING WIRES, A CENTRAL CHANNEL FOR ILLUMINATION, SUCTION AND INJECTION AND A LATERALLY DISPOSED BORE FOR FEEDING FLUIDS

[75] Inventor: Mikio Utsugi, Machida, Japan

[73] Assignee: Olympus Optical Co., Ltd., Tokyo, Japan

[21] Appl. No.: 873,779

[22] Filed: Jan. 31, 1978

[30] Foreign Application Priority Data

Jan. 31, 1977 [JP] Japan .................. 52/10194[U]

[51] Int. Cl.² .................. A61B 1/06; A61B 1/12; A61B 1/30
[52] U.S. Cl. ...................... 128/6; 128/328; 128/7; 128/8
[58] Field of Search .................. 128/4-8, 128/319, 320, 328, 340, 345, 242-244, 303.11, 303.15, 303.16, 356, 346

[56] References Cited

U.S. PATENT DOCUMENTS

| 3,610,231 | 10/1971 | Takahashi et al. | 128/6 |
| 3,791,387 | 2/1974 | Itoh | 128/320 |
| 4,046,149 | 9/1977 | Komiya | 128/328 |
| 4,046,150 | 9/1977 | Schwartz et al. | 128/328 |
| 4,108,211 | 8/1978 | Tanaka | 128/4 X |

*Primary Examiner*—Robert W. Michell
*Assistant Examiner*—Jeffrey W. Tayon

[57] ABSTRACT

An apparatus for removing a foreign matter from the human body cavity includes a sheath to be inserted into the body cavity, a foreign matter trapping section and a device for selecting the flexing length of the flexing portion of the sheath. The sheath is made of a flexible material, and the foreign matter trapping section comprises a ring member disposed at the front end of the sheath and trapping wires extending through the lateral side wall of the sheath with their corresponding ends connected to the ring member in circumferentially spaced relation and their other ends individually movable longitudinally of the sheath. By individually operating the trapping wires a foreign matter within the body cavity can be positively caught by or held within a cage defined by the trapping wires. The flexing length selection device can properly adjust the flexing length of the flexing portion of the sheath to be inserted into the body cavity.

11 Claims, 9 Drawing Figures

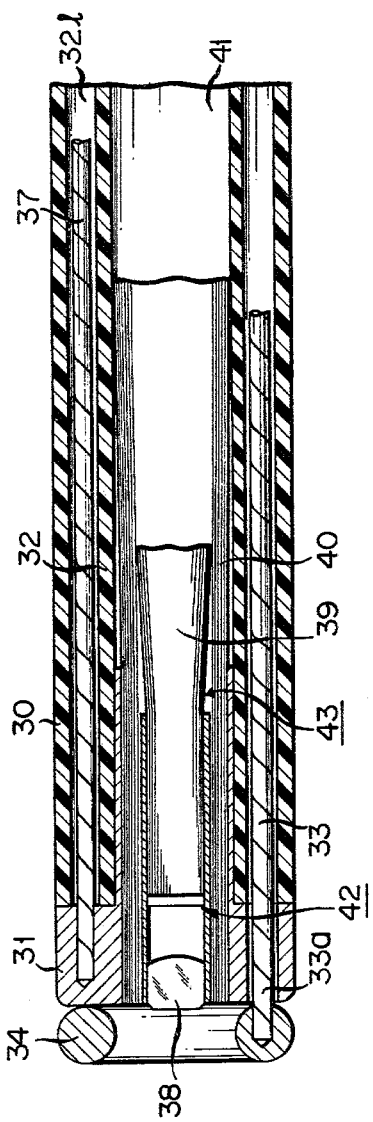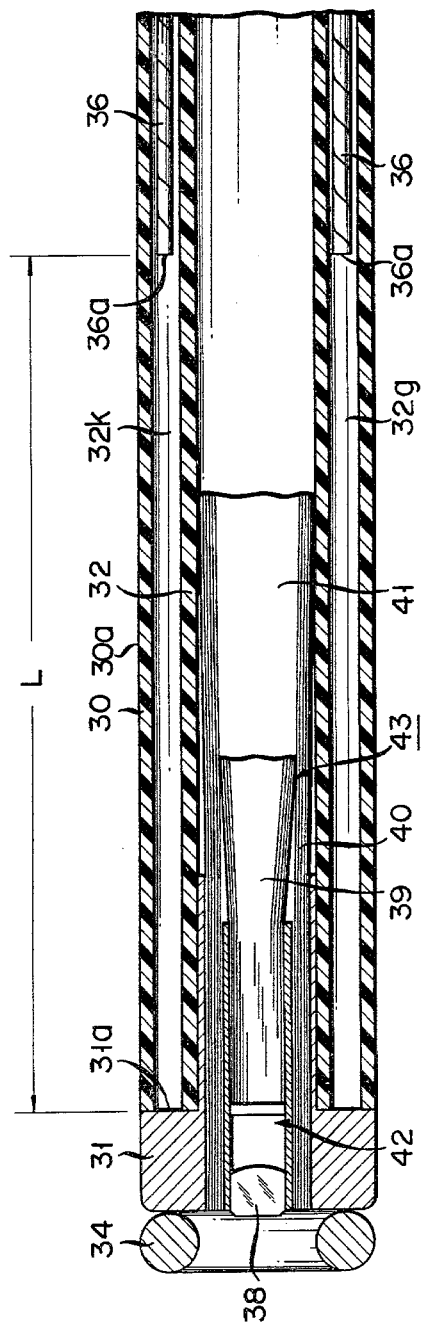

APPARATUS FOR REMOVING A FOREIGN MATTER HAVING INDIVIDUALLY OPERABLE TRAPPING AND FLEXING WIRES, A CENTRAL CHANNEL FOR ILLUMINATION, SUCTION AND INJECTION AND A LATERALLY DISPOSED BORE FOR FEEDING FLUIDS

BACKGROUND OF THE INVENTION

This invention relates to an apparatus for removing a foreign matter, such as a stone or calculus in the choledochus and ureter, from within the human body cavity.

Conventionally, an incision is necessary to remove a stone or calculus in the narrow human body cavity or duct such as the choledochus. A recent advance of endoscope technique permits such a stone to be removed orally. The removal of a stone in the choledochus, for example, is effected as follows. As shown in FIG. 1, a duodenofiberscope 1 is lowered, from the mouth of the opening of a common bile duct 2 which is open through pappila vateri into the duodenum. The opening of the common bile duct 2 is cut and enlarged by an electrosurgical instrument 3 which is inserted thereinto through the channel of the duodenofiberscope 1. After withdrawing the instrument 3 from the duodenofiberscope 1, a sheath of a cage type stone removing device 5 is inserted, as shown in FIG. 2, through the channel of the duodenofiberscope 1 and the incised opening of the common bile duct 2 into that region of the choledochus 6 where a stone 7 to be removed is located. A cage or basket 8 of the stone removing device 5 is extended from the front end of the sheath and expanded. Then, the cage 8, together with the sheath, is withdrawn toward the opening of the bile duct 2. During withdrawal, the stone 7 is trapped in the cage 8 or held by the wires and removed from the choledochus 6.

As shown in FIG. 3, the cage type stone removing device 5 comprises the cage 8 and the sheath 10. The cage 8 comprises a plurality of spiral, elastic and flexible wires 9, a first connecting member 12 by which the front ends of the wires 9 are bundled, and a second connecting member 13 by which the rear ends of the wires 9 are bundled. To the connecting member 13 is connected the front end of an operating wire 11 which passes through the central bore of the sheath 10 and is reciprocably movable longitudinally of the sheath 10 when operated at the control section of the dudenofiberscope 1.

While the sheath 10 is being inserted into the intended portion of the choledochus 6, the cage 8 is received within the bore of the flexible sheath 10. After the insertion of the sheath is completed, the operating wire 11 is moved forwardly of the sheath 10, causing the cage 8 to be extended from the distal end of the flexible sheath 10 so that it expands, as shown in FIGS. 2 and 3, due to its elastic force. This permits the stone 7 to be trapped within the cage 8.

The above-mentioned operation applies to the removal of a stone in the other body cavity such as the ureter.

Suppose that under observation by an X-ray fluoroscope a stone removing operation is effected using a conventional stone removing device. In this case, the arrangement or configuration of the cage when it is extended from the sheath is determined by the position of the cage within the sheath and there is little possibility that the stone will be exactly situated between the adjacent trapping wires of the cage. If the stone rides on the wire of the cage, it is necessary to withdraw the cage into the sheath, make a suitable adjustment such as some rotation around the axis of the cage, and again extend it out of the sheath for stone removal. Such operations are cumbersome, time-consuming and undesirable from the standpoint of the protection of the body cavity. Furthermore, the bore of the sheath of the conventional cage type stone removing device is exclusively used for the reception of the cage and as a channel for the operating wire and it is not used for the other objects.

SUMMARY OF THE INVENTION

An object of this invention is to provide apparatus for removing a foreign matter from a human body cavity, in which trapping wires can be individually extended from and withdrawn into the forward end portion of the sheath such that a stone in the body cavity can be trapped in the cage or held by the trapping wires.

Another object of this invention is to provide apparatus for removing a foreign matter from a human body cavity, which can vary the flexing length of the flexing portion of a sheath by adjusting a distance between the front end of rigid rod members inserted into the flexible sheath and the distal end of the sheath.

Another object of this invention is to provide apparatus for removing a foreign matter from the human body cavity, which includes a sheath having a lateral wall through which trapping wires, rigid rod members and flexible wires can pass and a central bore which can receive an optical system for observation and illumination as well as serve as a fluid feeding channel and/or a fluid sucking-in channel.

According to this invention, there is provided apparatus for removing foreign matter from the body cavity which comprises a flexible sheath having a hollow cylindrical central channel formed therein, a ring member disposed at the distal end of the sheath and elastic, flexible trapping wires extending lengthwise in the sheath and having ends adjacent to the distal end of the sheath connected to the ring member in spaced relation to each other. The trapping wires are adapted to be movable separately lengthwise of the sheath.

In the sheath, there is provided an adjusting means for selecting a flexing length of the flexing portion of the sheath.

The adjusting means may comprises flexing rods for bending the sheath and rigid rod members having their front ends separated from the distal end of the sheath at a desired length so as to select the flexing length of the flexing portion.

The trapping wires and adjusting means are provided in the lateral wall of the sheath such that the central channel can receive an optical system for observation and illumination, and/or serve as a fluid feeding channel and/or a sucking-in channel.

BRIEF DESCRIPTION OF THE DRAWINGS

FIG. 5 is a cross-section as taken along line 5—5 of FIG. 4;

FIG. 6 is a cross-section as taken along line 6—6 of FIG. 4;

DETAILED DESCRIPTION OF THE PREFERRED EMBODIMENTS

Figure 1:
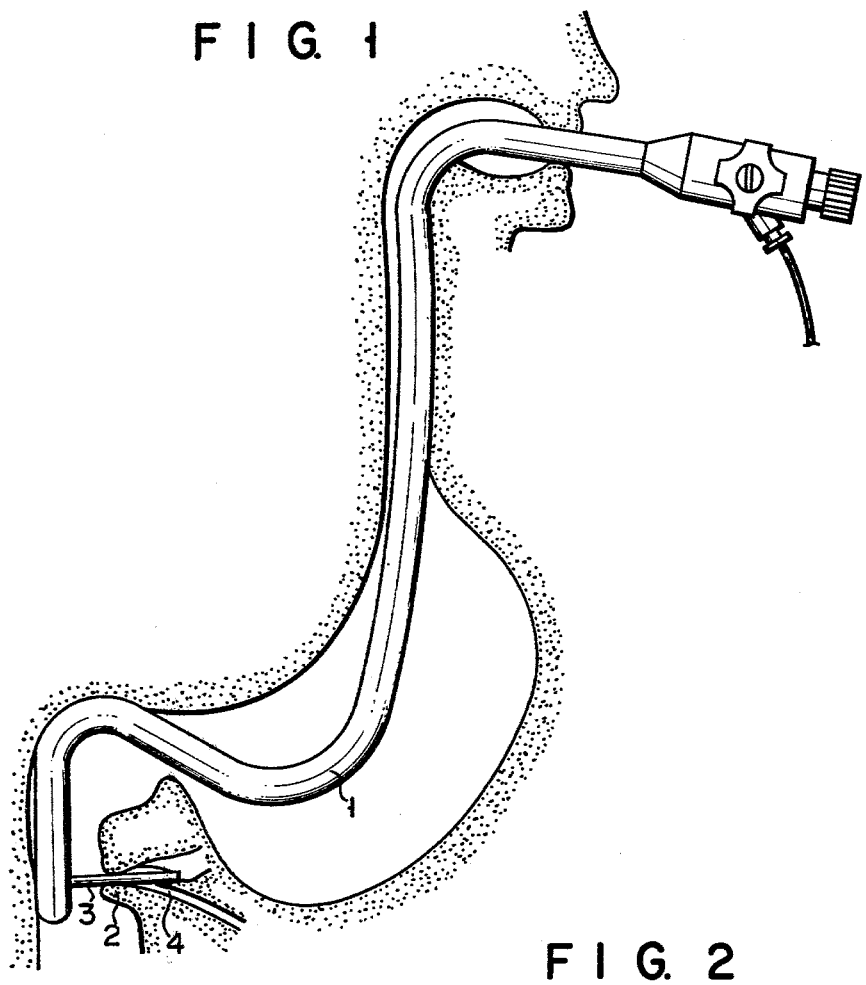
FIG. 1 is a view showing the state in which the opening portion of a common bile duct is cut and enlarged by an electrosurgical instrument, before a stone removing device can be used.
Figure 2:
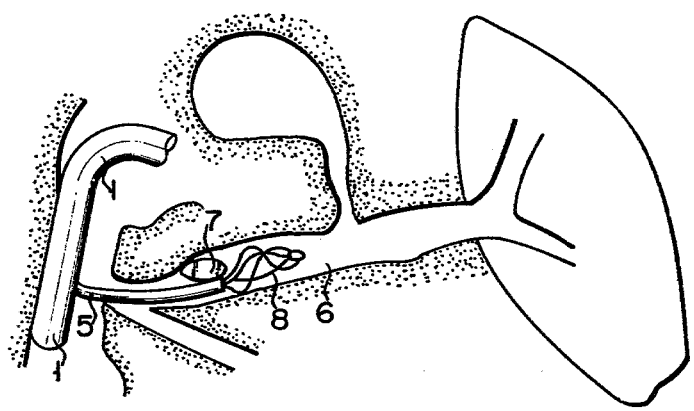
FIG. 2 is a view showing the state in which a stone is being removed from the choledochus by a conventional cage-type stone removing device.
Figure 4:
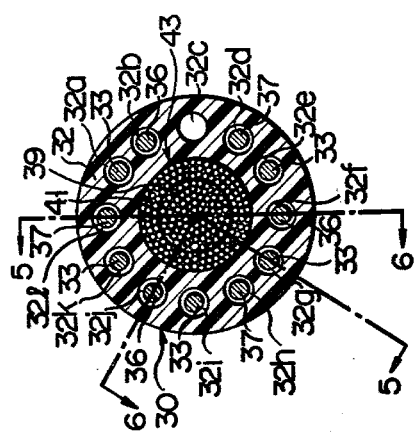
FIG. 4 is a transverse cross-section showing a main part of a stone removing device according to this invention.
Figure 7:
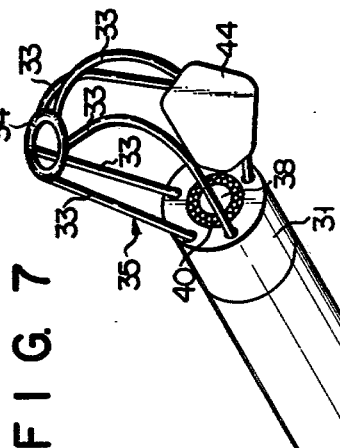
FIG. 7 is a perspective view showing in an operative state the front end of a flexible sheath of the stone removing device of FIG. 4.

Referring to FIGS. 4 to 6, apparatus for removing foreign matter from the body cavity (hereinafter referred to as "a stone removing device") includes a sheath 30 which is a hollow, cylindrical member made of flexible plastic material, and which is adapted to be inserted into a human body cavity including a duct such as the choledochus. An annular rigid head portion 31 is secured to the distal end portion of the sheath 30. Small axial small bores 32a, 32b, 32c, 32d, 32e, 32f, 32g, 32h, 32i, 32j, 32k, 32l extend through a lateral wall 32 of the sheath 30 in a manner circumferentially equidistantly spaced apart from each other. Front ends 33a of elastic and flexible trapping wires 33 pass through the small bores 32a, 32e, 32g, 32i and 32k, respectively, and are connected to a ring connecting member 34 in front of the head portion 31 of the sheath 30 at the positions corresponding to the circumferential positions of the small bores 32a, 32e, 32g, 32i and 32k. The trapping wires 33 can be individually operated at the rear ends so as to cause the front ends 33a of the trapping wires 33 to be drawn into and extended out of the sheath 30. The, the trapping wires 33, together with the connecting member 34, constitutes a cage or basket 35 as shown in FIG. 7. Inserted into the bores 32b, 32f and 32j are rod members 36 which are much more rigid than the trapping wires 33 and flexing wires as will be described later. The rod members 36 are moved along the respective bores at the proximal end of the sheath 30 or at the operation section of an endoscope into which a stone moving device of this invention is inserted such that the front ends 36a of the rod members 36 can be separated from the rear end 31a of the head portion 31 at a desired distance L, as shown in FIG. 6. The portion of the sheath 30 which is in the range indicated by L is defined as a flexing portion 30a. The length L of the flexing portion 30a is selectively determined by the depth of the small duct or tract into which the flexing portion 30a is inserted. The flexing portion 30a of the sheath 30 can be easily bent as desired, as will be described later. But the remaining portion of the sheath 30 into which the rod members 36 are inserted is hardly bent due to the rigidity of the rod members 36. The positive insertion of the sheath 30 into a small duct or tract such as the choledochus can be assured by freely adjusting the flexing length of the flexing portion 30a.

The flexing wires 37 are inserted into the respective small bores 32d, 32h and 32l and have their front ends secured to the head portion 31. The flexing portion 30a can be bent into a desired shape by individually pulling the rear ends of the flexing wires 37. The small bore 32c is connected at the proximal end to a pump, not shown, and serves as a channel for feeding fluid such as a contrast medium, dye, liquid medicine, physiological sodium chloride solution, and diluent for body fluid and-/or as a channel for sucking in a plasma, nucus, etc. in the body cavity.

A compound objective lens 38 is mounted in the center of the head portion 31 and a bundle of image guide optical fibers 39 is optically connected at the front end thereof to the lens 38. The bundle 39 is inserted into a central cylindrical bore 41 of the sheath 30 in a manner to be surrounded with an illumination optical system comprising a bundle of light guide optical fibers 40. The lens 38 and fiber bundle 39 constitute an observation optical system 42. The system 42 and illumination fiber bundle 40 constitutes an optical system 43 for observation and illumination. It is desirable that the system 43 be inserted into and removed from the central cylindrical bore 41 at the proximal end of the sheath 30. In this case, an eyepiece or an ocular is provided at the proximal end of the stone removing device.

In operation, the sheath 30 of the stone removing device is inserted, either singly or through an endoscope, into the body cavity region of interest with the trapping wires 33 completely inserted into the sheath 30. While observing the observation optical system 42 under illumination of the illumination optical system, the flexing wires 37 and rod members 36 are operated such that the flexing angle and flexing length L of the flexing portion 30a of the sheath 30 are adjusted to bring the distal end of the sheath 30 at that region of the body cavity where a stone or calculus 44 exists.

Then, the trapping wires 33 are individually operated. In this case, those trapping wires 33 at the side of the stone 44 are extended farther than the rest of the trapping wires 33 to cause them to be outwardly curved, as shown in FIG. 7, to permit the adjacent trapping wires 33 facing the stone 44 to be separated to a greater extent from each other so that the stone 44 is situated therebetween. Thereafter, the trapping wires 33 facing the stone 44 are withdrawn, allowing the stone 44 to be trapped within the cage 35. After the stone 33 is trapped, all the trapping wires 44 are operated to extend from the distal end of the sheath 30 by substantially the same length such that the cage 35 assumes a substantially cylindrical shape. In consequence, the stone 44 is completely trapped in the cage 35 and will not be dropped therefrom. If the stone 44 trapped within the cage 35 is too large, there is a risk that it will injure the inner surface of the body cavity region, when it is forcefully taken out of the body cavity region. In this case it is necessary that the stone 44 be left in the body cavity region until an operation including further incision for widening the opening of the narrow body cavity such as the choledochus is effected.

In such a case, a pair of adjacent trapping wires 33 are projected from the distal end of the sheath 30 farther than the rest of the trapping wires 33, or the rest of the wires 33 are withdrawn into the sheath 30, or said pair of trapping wires 33 are projected from the distal end of the sheath 30 as well as the rest wires 33 are withdrawn into the sheath 33, causing said pair of trapping wires 33 to be spread wide apart and dropping the stone 44 out of the cage 35 into the body cavity region. Such an operation can not be effected by the conventional stone removing device. According to this invention, therefore, safety to the body cavity is enhanced.

Where a cage of the conventional stone removing device is projected out of the sheath, it is radially outwardly expanded due to the resilient force outwardly applied to trapping wires. If, however, this projection of the cage is repeated, such an expansion force is gradually lessened and the cage cannot be expanded, with the result that it will be difficult to trap a stone within the cage. According to this invention it is not necessarily required that the trapping wires 33 be outwardly expanded by their own force when they are projected out of the sheath 30. By adjusting the projected lengths of the trapping wires 33 from the sheath 30, the trapping wires 33 can be bent outwardly to a required extent, and a pair of adjacent trapping wires 33 facing the stone 44 can be positioned and separated from each other for such a distance that the stone 44 passes therethrough. Accordingly, the stone 44 can be readily and positively trapped within the cage 35.

In the embodiment of FIGS. 4 to 7, the connecting member 34 to which the front ends of the trapping wires 33 are connected is a ring and has a through hole at its central portion, the connecting member 34 gives no obstruction to the observation of the body cavity region by the optical system 43. Therefore, the sheath 30 can be inserted into a very small body cavity branch duct or tract of the human body by using the optical system 43 together with a flexing mechanism comprising the rod members 36 and flexing wires 37. The connecting member 34 is not restricted to such ring-like shape and may take a horseshoe shape or a U-shape. In this case, the same object can be attained as in the case of the ring-like shape.

Figure 8:
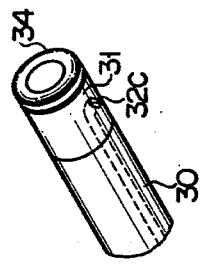
FIG. 8 is another embodiment of a stone removing device according to this invention.
Figure 3:
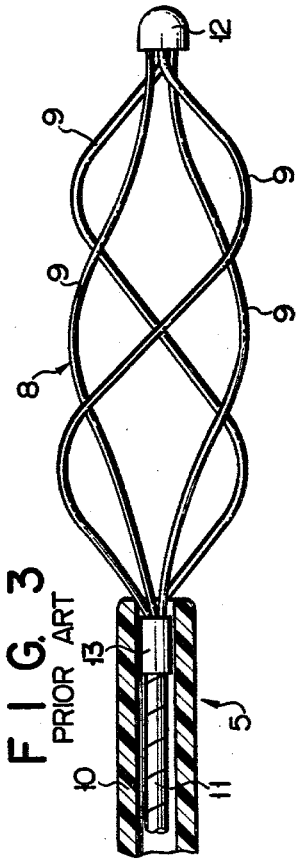
FIG. 3 is a longitudinal cross-section showing a main part of the conventional cage-type stone removing device.

FIG. 8 shows a modified form of the member 34. The member 34 of FIG. 8 is substantially O-shaped in configuration and a bore 32c used as a channel for feeding fluid opens on the lateral peripheral surface of the head portion 31.

Figure 9:
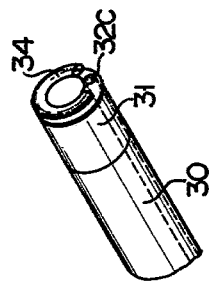
FIG. 9 is a further embodiment of a stone removing device of this invention.

FIG. 9 shows a modified form of a member 34. The member 34 of FIG. 9 is substantially horseshoe-shaped in configuration, and a bore 32c used as a channel for conducting fluid opens on that end surface portion of the head portion which is situated between the both ends of the horseshoe-shaped member 34.

Where the stone removing device is properly introduced into the body cavity by, for example, an X-ray fluoroscope, the central cylindrical bore 41 in the flexible sheath 30 can be, like the bore 32c, to inject a liquid such as a contrast medium, dye, liquid medicine, physiological sodium chloride solution and diluent for body fluid (for permitting easy observation) into the body cavity region of interest by by a pump provided at the proximal end of the bore 31 of the sheath 30. In addition or alternatively, a suction means may be provided at the proximal end of the bore 41 of the sheath 30 so as to suck in the body fluid in the body cavity and to permit the stone 44 to be readily trapped within the cage 35 a negative pressure produced in the bore 41. Particularly, when such suction means is used, the stone is positively brought into the cage 35 and in consequence a higher stone removing efficiency is obtained than when the stone 44 is trapped by the cage 35 alone. When the optical system 43 is detachably fitted in the bore 41 of the sheath 30, the bore 41 can be used as a channel for injecting liquid into the body cavity region and for sucking in a body fluid, stone, etc. present in the body cavity as well as a bore for receiving the optical system 42.

At least three flexing wires 37 extend through the lateral wall 32 of the sheath 30 and they are arranged at substantially equal intervals along the circumference of the sheath 30. Now suppose a plane including the axis of the sheath 30 before and after the flexing portion 30a is bent. If one of the wires 37 is present in the above-mentioned plane and at the side toward which the flexing portion 30a is to be bent, the flexing portion 30a can be freely bent by pulling only said one wire 37. Generally, however, there is little possibility that said one wire 37 is disposed in said plane. In this case, a pair of flexing wires 37, which are disposed opposite to each other with respect to said plane and are located at the side toward which the flexing portion 30a is to be bent, are properly pulled. The resultant force produced by the paired wires 37 bends the flexing portion 30a of the sheath 30 in the required direction to a required extent, without exerting any greater pulling forces on the paired wires 37.

What is claimed is:

1. Apparatus for removing foreign matter from a body cavity comprising:
   an elongated sheath made of flexible material and having bores extending through a lateral wall thereof;
   a hollow cylindrical central channel extending through the sheath;
   a connecting member disposed at a distal end of the sheath and provided at a center thereof with an opening larger than the diameter of the central channel of the sheath; and
   a plurality of elastic, flexible trapping wires passing through respective ones of said bores so as to be individually movable lengthwise of the sheath, said trapping wires having ends at the distal end of the sheath connected to the connecting member in a circumferentially spaced relation to each other.

2. The apparatus according to claim 1, wherein a plurality of flexing wires for bending the sheath extend through in the sheath, said flexing wires having corresponding ends thereof connected to the distal end of the sheath in a circumferentially spaced relation.

3. The apparatus according to claim 2, wherein said flexing wires extend through the lateral wall of the sheath.

4. The apparatus according to claim 3, wherein a plurality of rod members more rigid than the flexing wires extend through the lateral wall of the sheath and are movable along the sheath for defining a length of a flexing portion of the sheath between the distal end of the sheath and forward ends of the rod members.

5. The apparatus according to claim 4, wherein said rod members extend through the lateral wall of the sheath in a circumferentially spaced relation.

6. The apparatus according to claim 5, wherein said central channel receives an optical system for observation and illumination.

7. The apparatus according to claim 5, wherein said optical system comprises an objective compound lens, a bundle of image guide fibers optically connected thereto and a bundle of light guide fibers surrounding the bundle of the image guide fibers.

8. The apparatus according to claim 7, wherein said optical system is removable from the central channel in the sheath.

9. The apparatus according to claim 5, wherein said channel comprises a fluid feeding channel.

10. The apparatus according to claim 5, wherein said channel comprises a sucking-in channel.

11. The apparatus according to claim 1, wherein said connecting member comprises a ring member.

* * * * *